United States Patent [19]

Marteau D'Autry

[11] Patent Number: 5,417,123
[45] Date of Patent: May 23, 1995

[54] AUTOMATIC FILTERING AND IDENTIFICATION OF SAMPLES

[76] Inventor: Eric Marteau D'Autry, 1, rue Boutarel, 75004 Paris, France

[21] Appl. No.: 25,594

[22] Filed: Mar. 3, 1993

[30] Foreign Application Priority Data

Mar. 4, 1992 [FR] France .................. 92 02600

[51] Int. Cl.$^6$ ............................. G01N 35/00
[52] U.S. Cl. .................. 73/864.25; 73/864.86; 73/864.21
[58] Field of Search ........... 73/864.85, 864.25, 864.21, 73/864.81, 864.86, 864.87, 863.23, 863.24, 863.25, 864.91

[56] References Cited

U.S. PATENT DOCUMENTS

| | | | |
|---|---|---|---|
| 3,985,032 | 10/1976 | Avakian . | |
| 4,766,082 | 8/1988 | Marteau D'Autry | 73/863.32 X |
| 4,974,458 | 12/1990 | Koike | 73/864.25 X |
| 4,974,460 | 12/1990 | Baxter | 73/864.91 |
| 5,036,001 | 7/1991 | Gork et al. | 73/864.24 X |
| 5,055,263 | 10/1991 | Meltzer | 73/864.25 X |
| 5,102,623 | 4/1992 | Yamamoto et al. | 73/864.25 X |
| 5,216,926 | 6/1993 | Lipscomb | 73/864.25 |
| 5,305,650 | 4/1994 | Koike et al. | 73/864.21 |
| 5,306,510 | 4/1994 | Meltzer | 73/864.25 X |

FOREIGN PATENT DOCUMENTS

| | | |
|---|---|---|
| 0143097 | 5/1985 | European Pat. Off. . |
| 0339429 | 11/1989 | European Pat. Off. . |
| 0403905 | 12/1990 | European Pat. Off. . |
| 0438136 | 7/1991 | European Pat. Off. . |
| 0180511 | 5/1986 | France . |
| 3223589 | 12/1983 | Germany . |
| WO83/01912 | 6/1983 | WIPO . |

*Primary Examiner*—Thomas P. Noland
*Attorney, Agent, or Firm*—Mason, Kolehmainen, Rathburn & Wyss

[57] ABSTRACT

The present invention provides an XYZ type laboratory robot to be used with various peripherals suitable for analyzing and/or preparing samples of liquid. The robot has a work surface (1) including a moving system (2) for supporting elements (7) required for analyzing and/or preparing the samples of liquid. The work surface is associated with an appropriate sample-taking device such as a needle (5) connected to an automatic syringe and displaced vertically on appropriate sampling arms (3, 4) so that the needle (5) can be displaced along three orthogonal axes X, Y and Z. The needle (5) can be inserted into an appropriate stopper member (8) temporarily secured to the elements (7) such that a bottom portion of the needle (5) actively cooperates with the stopper member (8) resulting in the stopper member (8) exerting frictional forces on the outside of the bottom portion of the needle (5) to temporarily connect one of the elements (7) to the needle (5). When the needle (5) is so inserted into the stopper member (8), the element (7) can be displaced from any point on the work surface (1) to other determined points relative to the work surface (1) by programming the movement of the needle (5). Additionally, the XYZ type laboratory robot can be provided with an identifying device to identify the elements (7) being displaced and/or filtering elements (11) that each include a filtering device (10) for filtering the samples of liquid injected into the element (11).

8 Claims, 3 Drawing Sheets

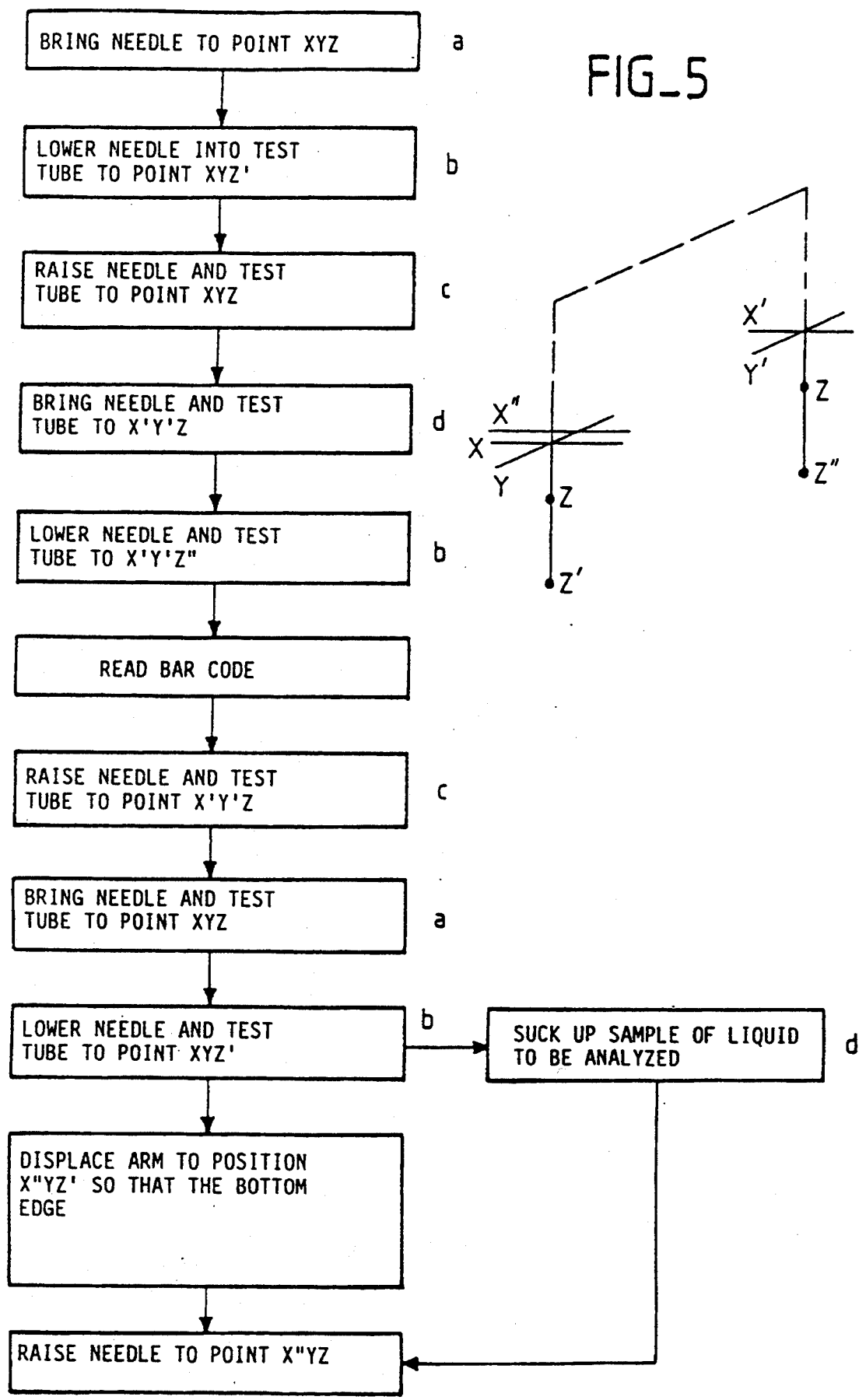

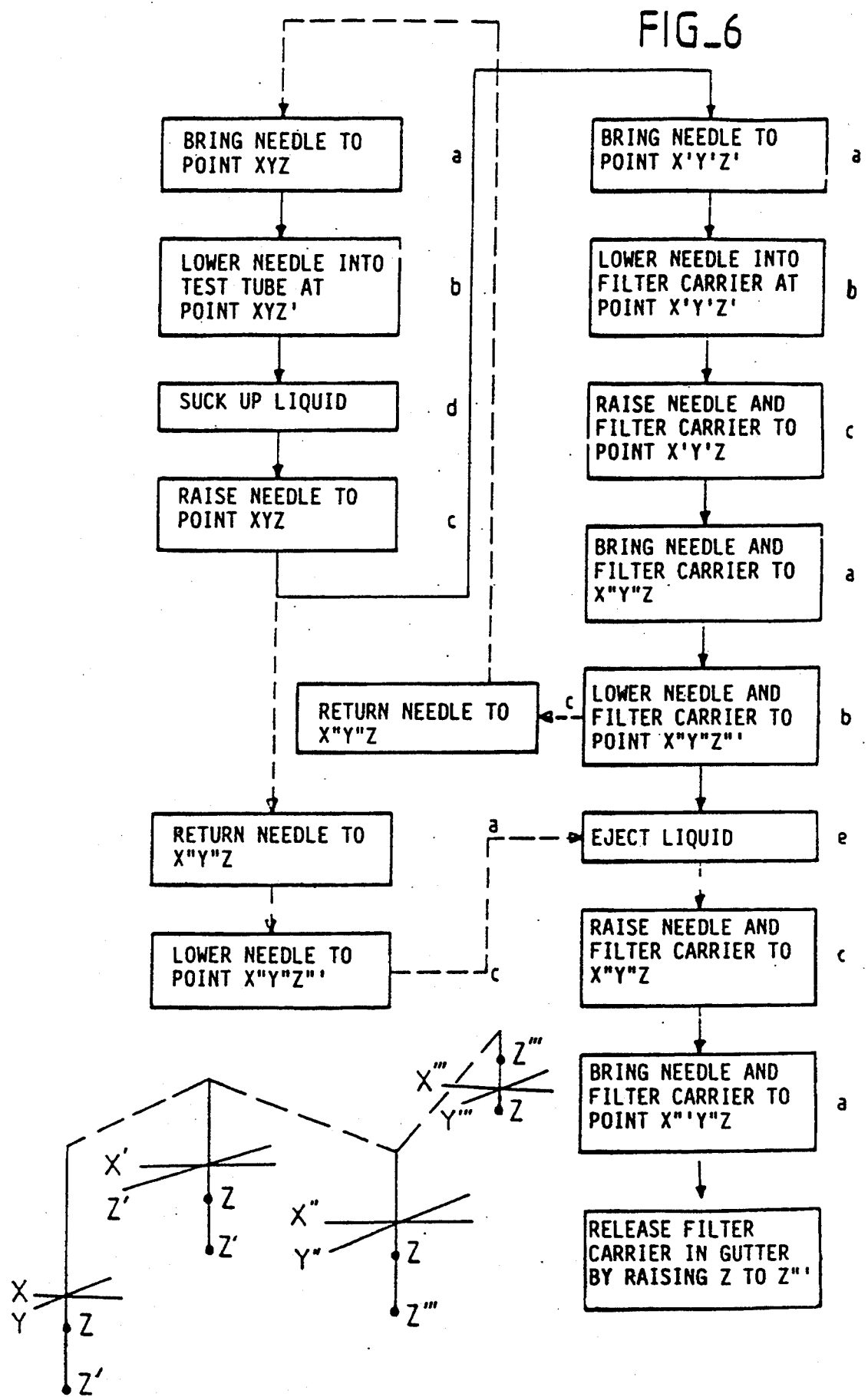
FIG_6

AUTOMATIC FILTERING AND IDENTIFICATION OF SAMPLES

The present invention relates to automating the transport of items required for analysis and to automating the identification of samples by automatic laboratory equipment for analyzing and/or preparing liquid samples.

BACKGROUND OF THE INVENTION

In general, automatic laboratory equipment for analyzing and/or preparing liquid samples comprises: a computerized central unit that controls various peripherals, such as the feed to a chromatography column, a signal detector at the outlet from the column, and data processing software, for example; and for automating the work of analysis and/or of preparation, a work surface that supports means for supporting the items required for analysis and/or preparation purposes, associated with a sample-taking device capable of transferring liquid from one receptacle to another in a pre-established order under the control of the central unit, the two receptacles being situated on the work surface.

Sample-taking devices are generally constituted by a needle connected to an automatic syringe disposed vertically on a sample-taking arm guided by the central unit in horizontal displacement over the work surface using predefined coordinates, and vertically so as to dip into the liquid to be sampled in the receptacle. Such devices are referred to as XYZ robots, because of their ability to displace the needle in three dimensions.

When the needle is in its low position, the central unit then causes the syringe to suck in or to eject the liquid, depending on whether a sample is to be taken from a receptacle or is to be ejected into another receptacle.

The various receptacles are generally tubes disposed in an array in order to facilitate entering three-dimensional coordinates for each receptacle into the central unit.

Such sampling and analysis systems, and the way in which they operate are described in the literature, and in particular in WO-A-83 04 325.

The automation of analyses has been improved by various systems for organizing the work surface, and in particular systems of carriers for elements for use in filtering and/or purifying samples, in particular the systems described in EP-A-0 180 511 (E. Marteau D'Autry).

The work surface is then fitted with first support means, e.g. supporting preparative cartridges, superposed on second support means, e.g. receiving firstly some test tubes and secondly a waste gutter.

The first support means are movable transversely over the second, and can be displaced linearly under drive from the sampling needle.

It has thus been observed that the needle of an XYZ robot is used not only as means for taking and ejecting liquid samples, but also as a means for imparting linear horizontal displacement to items placed on a carrier.

OBJECTS AND SUMMARY OF THE INVENTION

Although such XYZ robots have achieved a considerable degree of automation for the user, since their essential advantage lies in their ability to perform a large number of operations that are repetitive and tedious and that can be reproduced indefinitely, (such as taking a liquid sample and injecting it into a chromatography column), it is still necessary to improve the operation of XYZ robots, in particular to enable them to transfer items from one point to another of a work surface without it being necessary to make use of a carrier capable of limited displacement along a single horizontal axis.

Such displacement freedom thus necessarily requires it to be possible to displace items not only horizontally along a single axis, but also vertically and horizontally along an axis perpendicular to the first, i.e. in three dimensions X, Y, and Z.

To this end, it would be possible to imagine adding an automated arm to the XYZ robot and provided with suitable grasping means capable of taking an item for the purpose of transferring it to any previously-defined point of the work surface. Although easy to implement technically, such a solution nevertheless presents numerous drawbacks, particularly with respect to managing the work space and to the extra cost of adding such an arm.

Unexpectedly, it has been discovered that such displacements of objects in the three dimensions X, Y, and Z, can be obtained with robots but without adding special elements, merely by programming the means for controlling the needle to perform such a displacement, with the bottom end of the needle actively co-operating with an appropriate stopper member temporarily secured to the element to be displaced, the stopper member exerting the friction forces required on the outside of the bottom portion of the needle to obtain a temporary connection between the element to be transported and the needle, the grasping force proper being provided by the stopper member of the element to be displaced.

Such an appropriate stopper element may be a septum plug, as is commonly used for closing test tubes containing liquids to be analyzed.

In its center, a septum plug has a thin resilient circular wall that is easily pierced, said thin wall optionally being pre-pierced, so as to facilitate penetration of the needle of a syringe.

The diameter of the wall is less than the diameter of the needle, which must be forced through the plug. This force gives rise to an opposite reaction force from the circular edge of the wall and enables the septum plug to adhere to the needle, and consequently enables the element to be displaced to adhere to the needle.

As mentioned above, septum plugs are generally used for stopping test tubes containing samples to be analyzed. They may also be adapted to other elements that may be used in preparing samples for analysis, for example filter carriers or preparative chromatography columns.

When the septum plug is fixed on a test tube containing a liquid sample, the invention makes it possible to displace the test tube automatically from one point to another of the work surface.

It is common for such test tubes to be fitted with a label including a bar code for identification purposes. These labels are applied to test tubes before the liquid sample is taken for subsequent analysis in the laboratory. Merely by reading the bar code using an appropriate reader means, it is subsequently possible to recover all of the information required for identifying the sample to be analyzed, and in particular its origins.

In a particular embodiment of the present invention, it is thus possible to position a bar code reader on the work surface, thereby enabling the automatic machinery to identify the liquid sample before performing any operation such as purification, filtering, or analysis.

Thus, the automatic machinery can take a test tube from its sample carrier, move it up to the bar code reader for identification purposes, and then put it back in its initial place.

Thereafter, it can suck up liquid, remove the needle from the test tube, place it at some other appropriate point over the work surface, and eject the liquid so as to cause it to be subjected to a subsequent operation, e.g. such as high pressure liquid chromatography (HPLC).

When the liquid to be analyzed has solid impurities that may be harmful to subsequent analysis thereof, it must be filtered. The usual practice is to place a filter on a second test tube, with the automatic equipment taking a sample of liquid and injecting it into the filter prior to sucking up the liquid again from the second test tube.

In the prior art, and in particular in patent application EP-A-0 180 511, it is necessary to begin by positioning the filter on a moving carrier capable of being displaced transversely over a test tube or a draining rack.

According to the present invention, when the top of the filter carrier is fitted with a septum plug, it is possible to define a filter-carrier storage area on the work surface and a gutter for recovery after use, the automatic equipment being capable, if necessary, of retrieving a filter carrier from a storage area, of placing it on a special test tube, of releasing liquid into the filter carrier, of withdrawing it when all of the liquid has been treated, and finally of retrieving the filter carrier and taking it to the gutter where it is released and recovered.

The present invention also relates to a moving element designed to be placed on the work surface of an XYZ type robot as defined above, and fitted at its top end with an appropriate abutment which is temporarily secured thereto, and co-operating with the outside of the bottom portion of the robot's needle to serve as means enabling the moving element to be displaced from one point to another over the work surface by means of the needle.

Advantageously, the appropriate abutment is a stopper member, preferably a plug of the above-defined septum plug type.

The moving elements in accordance with the invention are preferably and generally test tubes provided with bar code labels, or filter carriers provided with filter elements.

BRIEF DESCRIPTION OF THE DRAWINGS

Accompanying FIGS. 1 to 6 enable the present invention to be better defined by means of preferred embodiments, but nevertheless without seeking to limit the scope of the invention.

Advantageously, the filter carrier is constituted by two hollow cones interconnected at their large bases via a filter element 10, the apexes of the cones being pierced to allow a liquid to pass, one of the ends serving as the base of the filter carrier and the other being designed to receive the appropriate stopper member 8.

Figure 1:
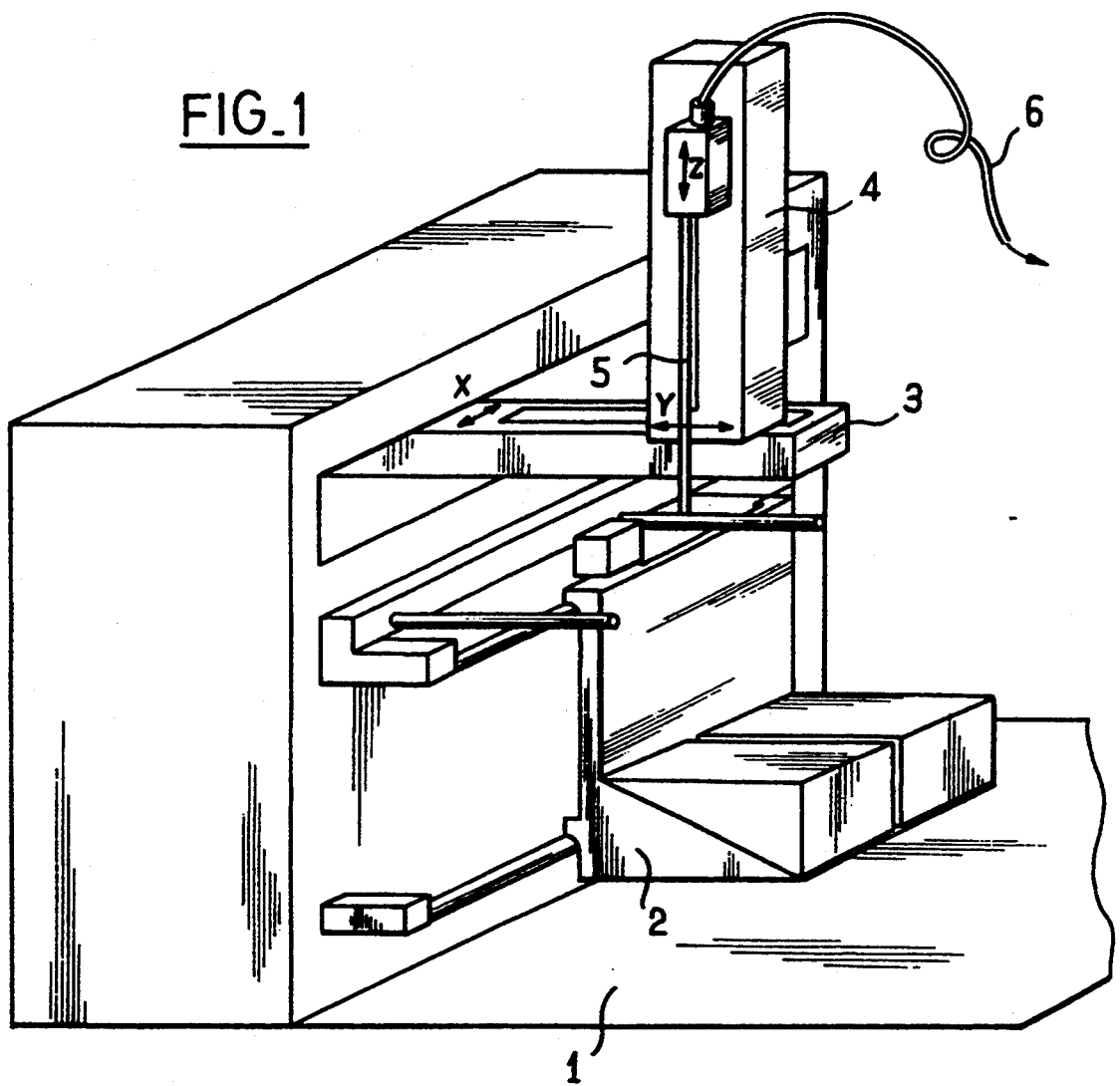
FIG. 1 shows the active portion of an XYZ robot including a work surface 1, a moving system 2 for supporting various elements, a horizontal arm 3 for supporting the needle, and providing horizontal X, Y displacements thereof, a vertical arm 4 supporting the needle and providing vertical Z displacements, and a sampling needle 5 connected to an automatic syringe via a capillary hose 6.
Figures 2, 3, 4:
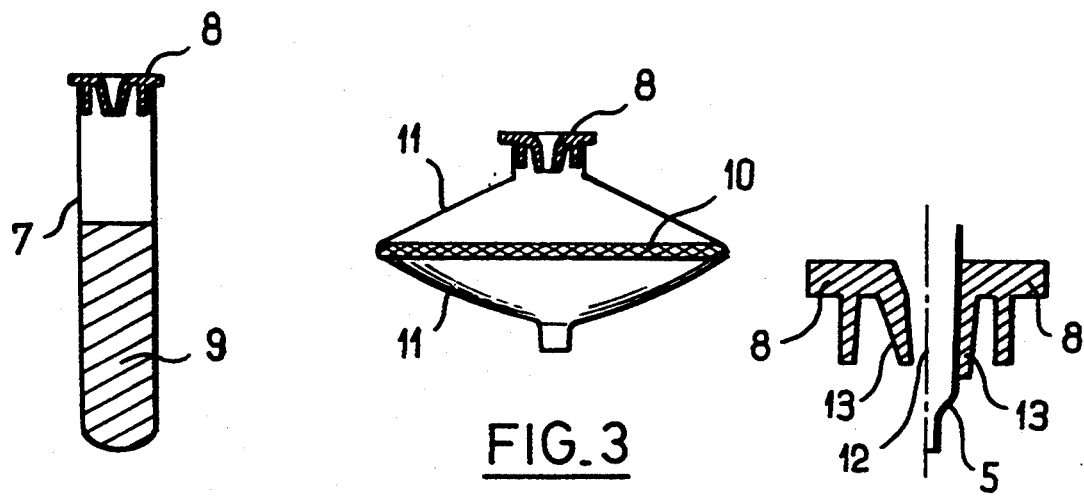
FIG. 2 is a section through a test tube 7 fitted with a septum plug 8 and having a sample of liquid 9.
FIG. 3 is a section view through a filter 10 and a filter support 11 fitted at the top with a septum plug 8.

FIG. 4 is a detailed section view of a septum plug 8, having a needle 5 passing therethrough. The stopper plug 8 has an axial orifice 12 in which the needle 5 is received on being lowered through the center of the plug (with the conical flare facilitating guidance of the needle as it moves down).

The dimensions of the axial orifice 12 and the resilience of the stopper 13 are selected in such a manner that when the needle has penetrated fully through the plug, the sealed closure obtained in this way provides sufficient force to enable the selected element to be displaced.

FIG. 5 is a flow chart of an automatic operation for identifying a sample in a test tube fitted with a bar code label.

FIG. 6 shows two possible flow charts for automatically filtering a liquid sample prior to analysis of the sample.

MORE DETAILED DESCRIPTION

As can be seen in FIGS. 5 and 6, the only requirement for implementing the present invention is the presence of transportable elements fitted with respective appropriate stopper elements.

For displacement operations of said elements, the automatic equipment performs the usual three fundamental displacement movements of the needle:

a/ positioning the needle at a point XYZ;

b/ lowering the needle to a point XYZ;

c/ raising the needle to a point XYZ or XYZ"; with said movement be repeated as often as necessary, XYZ being the coordinates of the bottom end of the needle.

The present invention thus also relates to a method of identifying a sample of liquid 9 contained in a test tube 7 by using an XYZ type robot as defined above, in which the test tube 7 fitted with a bar code label and with an appropriate stopper member 8 that is temporarily secured to its top end is transported by the sampling needle 5 of the XYZ robot by active co-operation between the bottom portion of the needle 5 and the appropriate stopper member 8, the test tube being transported from its support on the work surface 1 to a determined location of the work surface 1 that is fitted with means suitable for reading bar codes, and once the bar code has been read, the test tube is returned to its starting point.

Finally, the invention relates to a method of automatically filtering a sample of liquid 9 contained in a test tube, by using an XYZ type robot as defined above, in which the robot uses its sampling needle 5 to perform the following operations:

sucking up a sample of liquid 9 from a test tube 7;

transporting the filter carrier 11 provided at its top end with an appropriate stopper member 8 that is temporarily secured thereto from a determined storage area of the work surface 1 to a second test tube 7 situated at a determined point of the work surface 1;

ejecting the liquid 9 into the filter carrier 11 in such a manner as to cause the filtered liquid to be recovered in the second test tube 7; and transporting the filter carrier 11 of the second test tube 7 to a recovery gutter situated at a determined point of the work surface 1, where the filter carrier 11 is released.

The person skilled in the art will be capable of adapting existing automatic equipment, in particular to enable the needle to be withdrawn from the element to be transported once the desired transport operation has been performed, e.g. by fitting a retractable abutment on the moving needle-support arm, or by displacing the arm laterally before lifting the needle out of the test tube, or by having a fixed abutment that is high enough on the XY movement, or by any other means.

What is claimed and desired to be secured by Letters Patent of the United States is:

1. A computer controlled XYZ type laboratory robot comprising: peripheral means including at least one displaceable receptacle means for analyzing and/or preparing samples of liquid, a work surface including support means for said receptacle means, the work surface being associated with a sample-taking device comprising a needle connected to an automatic syringe and disposed on sampling arm means for displacing the needle along three orthogonal axes X, Y, and Z under the control of a needle control means, a portion of the needle actively co-operating with a stopper member temporarily secured to said receptacle means to be displaced, the stopper member exerting friction forces on the outside of a portion of the needle to temporarily connect the receptacle means to the needle such that said receptacle means is displaced from one point to another on the work surface by programming the needle control means to displace said needle.

2. An XYZ robot according to claim 1, wherein said stopper member is a closure member in the form of a septum type plug.

3. An XYZ robot according to claim 2, wherein the septum plug has a resilient circular wall in its center that is easily pierced.

4. An XYZ robot according to claim 3, wherein the resilient circular wall has a diameter that is smaller than that of the needle which is adapted to penetrate therethrough.

5. An XYZ robot according to claim 2, wherein the septum plug has a resilient circular wall that is pre-pierced in its center.

6. An XYZ robot according to claim 1, wherein said receptacle means to be displaced is selected from: test tubes that are empty; test tubes that contain a sample of liquid to be analyzed; and filter carriers that include a filter element.

7. An XYZ robot according to claim 1, wherein said receptacle means to be displaced is a test tube having a bar code label thereon.

8. An XYZ robot according to claim 7, including, at a determined point of the work surface, means suitable for reading bar codes.

* * * * *